United States Patent [19]

Bielefeldt et al.

[11] Patent Number: 5,087,747

[45] Date of Patent: Feb. 11, 1992

[54] PROCESS FOR THE PREPARATION OF TRIFLUOROMETHANESULPHENYL CHLORIDE

[75] Inventors: Dietmar Bielefeldt, Ratingen; Rudolf Braden, Odenthal; Albrecht Marhold, Leverkusen, all of Fed. Rep. of Germany

[73] Assignee: Bayer Aktiengesellschaft, Leverkusen, Fed. Rep. of Germany

[21] Appl. No.: 523,627

[22] Filed: May 15, 1990

[30] Foreign Application Priority Data

Jun. 7, 1989 [DE] Fed. Rep. of Germany ....... 3918545

[51] Int. Cl.$^5$ ............................................. C07C 313/08
[52] U.S. Cl. .................................................. 562/821
[58] Field of Search ............... 562/125, 821, 825, 826, 562/827, 828, 829, 834, 836

[56] References Cited

U.S. PATENT DOCUMENTS 3,132,182 5/1964 Richert et al. .
4,970,337 11/1990 Bielefeldt et al. ................... 562/829

OTHER PUBLICATIONS

Poole, "The Preparation of Properties and Certain Sulfinyl Chlorides", 1956.

Primary Examiner—Alan Siegel
Assistant Examiner—Margaret Argo
Attorney, Agent, or Firm—Sprung Horn Kramer & Woods

[57] ABSTRACT

Trifluoromethanesulphenyl chloride is prepared by reacting bis-(trifluoromethyl)disulfane in the liquid phase with chlorine in the presence of a strong acid.

2 Claims, No Drawings

PROCESS FOR THE PREPARATION OF TRIFLUOROMETHANESULPHENYL CHLORIDE

The invention relates to a process for the preparation of trifluoromethanesulfenyl chloride from bis-(trifluoromethyl)-disulfane.

Trifluoromethanesufenyl chloride is a universally applicable chemical which is employed, for example, for the preparation of organic intermediate products (see Gmelin, Handbuch der anorganischen Chemie [Handbook of Inorganic Chemistry], Supplement to the 8th edition, Volume 9, Part 1, page 165 (1973)).

It is known (see J.C.S. (London) 1953, page 3225) that trifluoromethanesulfenyl chloride can be obtained from bis-(trifluoromethyl)-disulfane and chlorine after irradiation with UV light for 10 to 14 days. Reaction times of this length are prohibitive for use on an industrial scale. It is also known (see German Offenlegungsschrift [German Published Specification] 3,741,309) that trifluromethanesulfonyl chloride is obtained from bis-(trifluoromethyl)-disulfane by reaction with chlorine and water, preferably in the presence of strong acids.

A process has now been found for the preparation of trifluoromethanesulfenyl chloride which is characterized in that bis-(trifluoromethyl)-disulfane is reacted in the liquid phase with chlorine in the presence of a strong acid.

The following are examples of suitable strong acids: sulfuric acid, nitric acid, phosphoric acid, fluorosulphonic acid and chlorosulfonic acid. The strong acid is preferably employed in the anhydrous form, but small amounts of water can be present, for example up to 10% by weight in sulfuric acid, up to 5% by weight in nitric acid, up to 3% by weight in phosphoric acid and up to 5% by weight in fluorosulfonic acid and chlorosulfonic acid.

The chlorine can be added to the process according to the invention in the liquid or gaseous state. In terms of stoichiometry, 1 mole of chlorine is required for the conversion of 1 mole of the disulfane. At least 0.8 mole, preferably at least 1 mole, of chlorine is, for example, employed per mole of the disulfane. In the upward direction the amount of chlorine is no longer critical. It is possible, for example, to employ up to 10 moles or more of chlorine per mole of the disulfane.

The strong acid can be employed in quantities of, for example, 0.1 to 20 parts by weight of acid per part by weight of the disulfane.

The process according to the invention can be carried out at, for example, temperatures within the range from $-18°$ to $+120°$ C. Temperatures within the range from $0°$ to $80°$ C. are preferred. It is often advantageous to carry out the reaction in closed vessels or under pressure (for example up to 100 bar) in order to suppress the escape of volatile constituents.

The process according to the invention can be carried out either continuously or discontinuously. The reaction time can be, for example, 12 to 48 hours.

If appropriate, the process according to the invention can also be carried out in the presence of a catalyst, for example in the presence of a perfluoroalkylsulfonamide.

The reaction mixture present after the reaction according to the invention can be worked up, for example, by first, if appropriate, removing chlorine still present, for example by distillation or blowing off with nitrogen, and then distilling the mixture.

Examples of suitable materials for the vessel for carrying out the process according to the invention are steel, Hasteloy®, glass, Teflon® and vessels lined with lead or enamel.

The process according to the invention is distinguished by the fact that it permits the preparation of trifluoromethanesulfenyl chloride in a simple manner and in substantially shorter reaction times than hitherto. This is decidedly surprising, since, according to the state of the art, irradiation with UV light has been considered necessary and another reaction product, namely trifluoromethanesulfonylchloride, has been obtained when stronq aqueous acids are used.

EXAMPLE

EXAMPLE 1

404 g of bis-(trifluoromethyl)-disulfane and 300 g of anhydrous sulfuric acid were initially placed in a Teflon-lined autoclave and were charged with a pressure of 5 bar of nitrogen. 100 ml of liquid chlorine were then metered into this solution at 40° C. in the course of 2 hours, and the reaction mixture was stirred for a further 48 hours at 40° C. Purification of the reaction product was effected by distillation. In the distillation 3.5 g of bis-(trifluoromethyl)-disulfane were recovered and 482 g of trifluoromethanesulfenyl chloride having a boiling point of 0° to 2° C. at normal pressure were isolated.

EXAMPLE 2

404 g of bis-(trifluoromethyl)-disulfane and 200 g of anhydrous trifluoromethanesulfonic acid were initially placed in a Teflon-lined autoclave and were charged with a pressure of 5 bar of nitrogen. 100 ml of liquid chloride was metered into this solution at 40° C. in the course of 2 hours, and the reaction mixture was then stirred for 48 hours at 40° C. Purification of the product was effected by distillation. In this distillation, 48 g of unreacted bis-(trifluoromethyl)-disulfane were recovered and 399 g of trifluoromethanesulfenyl chloride having a boiling point of 0° to 2° C. at normal pressure were isolated.

EXAMPLE 3

4,040 g of bis-(trifluoromethyl) -disulfane and 2,000 g of 96% strength sulfuric acid were initially placed in a 10 l Hasteloy autoclave and were charged at 18° C. with a pressure of 5 bar of nitrogen. 1,000 ml of liquid chlorine were pumped into this solution at 40° C. in the course of 2 hours. The reaction mixture was stirred for a further 12 hours at 40° C. and under a pressure of 14 to 16 bar, and it was then purified by distillation. 4,250 g of trifluoromethanesulfenyl chloride having a boiling point of 0° C. at normal pressure and 350 g of unreacted bis-(trifluoromethyl) -disulfane were obtained.

EXAMPLE 4 (for comparison)

101 g of bis-(trifluoromethyl)-disulfane and 200 ml of 70% strength sulfuric acid were initially placed in a Teflon-lined autoclave. 20 g of liquid chlorine were metered into this solution within the temperature range from 30° to 40° C., and the reaction mixture was stirred for a further 8 hours. The following were obtained after working up the reaction mixture by distillation:
83.7% by weight of unreacted bis-(trifluoromethyl)-disulfane,
14.0% by weight of trifluoromethanesulfenyl chloride and 2.3% by weight of trifluoromethylsulfonyl chloride.

What is claimed is:

1. A process for the preparation of trifluoromethanesulfenyl chloride in which bis-(trifluoromethyl)-disulfane is reacted at a temperature of from about −18° to +120° C., in the liquid phase with chlorine wherein at least 0.8 mole of chlorine is employed per mole of the disulfane, in the presence of an effective amount of a strong acid selected from the group consisting of sulfuric acid, nitric acid, phosphoric acid, fluorosulphonic acid and chlorosulfonic acid, in anhydrous form or in the presence of up to 10% water by weight of acid when said acid is sulfuric acid, up to 5% water by weight of acid when said acid is nitric acid, fluorosulfonic acid or chlorosulfonic acid, or up to 3% water by weight of acid when said acid is phosphoric acid.

2. The process of claim 1, in which 0.1 to 20 parts by weight of strong acid are employed per part by weight of the disulfane.

* * * * *